US00RE36020E

United States Patent [19]

Moore et al.

[11] E Patent Number: Re. 36,020

[45] Reissued Date of Patent: Dec. 29, 1998

[54] METHOD AND APPARATUS FOR TYING SUTURE TO BONE

[75] Inventors: Robert R. Moore, Hayward, Calif.; Arnold K. Cohn, Glenview, Ill.

[73] Assignee: Orthopedic Systems, Inc., Union City, Calif.

[21] Appl. No.: 547,645

[22] Filed: Oct. 5, 1995

Related U.S. Patent Documents

Reissue of:

[64] Patent No.: 5,250,055
Issued: Oct. 5, 1993
Appl. No.: 895,604
Filed: Jun. 8, 1992

[51] Int. Cl.[6] ..... A61B 17/00

[52] U.S. Cl. ..... 606/144; 606/148; 606/139; 606/96

[58] Field of Search ..... 606/1, 53, 60, 606/72, 80, 86, 96, 99, 103, 139, 148, 170, 171, 180, 222, 223, 232; 128/898, 772; 604/28; 623/13

[56] References Cited

U.S. PATENT DOCUMENTS

| | | | |
|---|---|---|---|
| 722,105 | 3/1903 | Hervey | 606/222 |
| 2,543,780 | 3/1951 | Hipps et al. | 606/86 |
| 2,725,053 | 11/1955 | Bambara | 606/96 |
| 4,590,929 | 5/1986 | Klein | 606/80 |
| 4,625,717 | 12/1986 | Covitz | 606/103 |
| 4,744,353 | 5/1988 | McFarland | 606/96 |
| 4,779,616 | 10/1988 | Johnson | 606/148 |
| 5,026,350 | 6/1991 | Tanaka et al. | 604/164 |
| 5,037,422 | 8/1991 | Hayhurst et al. | 606/232 |
| 5,037,433 | 8/1991 | Wilk et al. | 606/222 |
| 5,054,501 | 10/1991 | Chuttani et al. | 604/282 |
| 5,102,421 | 4/1992 | Anspach, Jr. | 606/232 |
| 5,234,443 | 8/1993 | Phan et al. | 606/148 |
| 5,250,054 | 10/1993 | Li | 606/148 |
| 5,281,238 | 1/1994 | Chin et al. | 606/148 |

FOREIGN PATENT DOCUMENTS

| | | | |
|---|---|---|---|
| 166102 | 11/1964 | U.S.S.R. | 606/222 |
| 172957 | 7/1965 | U.S.S.R. | 606/222 |
| 1115736 | 9/1984 | U.S.S.R. | 606/222 |

*Primary Examiner*—Michael Powell Buiz
*Assistant Examiner*—Tina T. D. Pham
*Attorney, Agent, or Firm*—Limbach & Limbach L.L.P.

[57] ABSTRACT

A method and apparatus for arthroscopic attachment of a suture to bone by drilling parallel holes in the bone with a cannula and drill guide and passing a suture down one hole through soft bone into the other hole and retrieving the suture through the second hole.

10 Claims, 3 Drawing Sheets

METHOD AND APPARATUS FOR TYING SUTURE TO BONE

Matter enclosed in heavy brackets [ ] appears in the original patent but forms no part of this reissue specification; matter printed in italics indicates the additions made by reissue.

BACKGROUND OF THE INVENTION

This invention relates to a method and apparatus for attaching sutures to bone and more particularly to doing so arthroscopically.

It is desirable to be able to attach a suture to bone with the suture encircling a portion of the hard material which forms the surface portion of the bone so that the strength of that hard portion of the bone forms a strong anchor for the suture. Apparatus for anchoring sutures in this way is sold by Orthopedic Systems Inc. under the name COHN Suture Fixation Device. That apparatus provides two intersecting drilled holes into the bone through which a suture can be passed, but it is not readily adapted to arthroscopic surgery because it requires that a large opening be made for access to the bone.

SUMMARY OF INVENTION

In accordance with this invention, a suture can be attached to the bone with the same final strength that is achieved with the COHN S.F.D. and the procedure may be performed arthroscopically. The procedure is performed by insertion of a small cannula to the bone through overlying sort tissue. A drill guide with at least two generally parallel bores is inserted in the cannula and used for drilling two parallel holes in the bone through the hard material near the surface of the bone down into the soft interior material of the bone. The two holes in the bone need not intersect.

A suture pusher is then inserted through one of the bores in the drill guide and operated to push a suture loop through the soft bone material from one hole to the other. The suture pusher may take the form of a scissors-like device or a thin flexible wire made from a strong resilient material such as a TiNi alloy with a 90° bend at one end for pushing the suture from one hole to the other. The suture pusher preferably has a laterally extending handle at one end extending in the opposite direction from the suture pushing end so that the surgeon knows what direction the suture pushing end extends.

The suture pushing end extends laterally from the stem of the suture pusher a sufficient distance to extend from one hole to the other through the bone, and the wire embodiment has a radius of curvature which is large enough that the wire will not break when the suture pushing end is resiliently deformed to near-straightness as it is inserted through the drill guide.

The suture pusher is provided with an eye to carry the suture or it may be provided with a notched end similar to that employed in the COHN S.F.V. so that when the suture pusher is inserted through one hole and passes to the other hole it carries the loop of the suture which may be retrieved through the second hole in the manner in which a suture is retrieved with a COHN S.F.D. Once the suture is in place extending into and out of the bone, the suture pusher and drill guide are withdrawn; knots may be tied in the suture and passed along the suture through the cannula to the bone; the ends of the suture clipped off and the cannula removed.

It may be possible to fix a suture using the drill guide alone without the cannula where the drill guide performs the function of the cannula, but it is preferred to use separate drill guides and cannulas so that knots can be passed down the suture to the bone while surrounding soft tissue is held back.

In this manner a suture can be attached to the bone firmly anchored by encircling the bridge of hard bone material between the two parallel drill holes, and the attachment is accomplished without leaving metal anchoring materials in the bone. The suture may be used for attaching any desired material to the bone as for instance where the end of a ruptured tendon may be initially held to the bone by the cannula and then attached to the bone by the suture.

In order to facilitate penetration of the suture pushing end of the wire suture pusher into the soft part of the bone before it resiliently resumes its curved shape and penetrates to the second hole, a tube may be inserted through one bore of the drill guide and into the hole drilled in the bone to guide the suture pusher to a predetermined depth in the bone before its tip emerges into the bone.

DETAILED DESCRIPTION

In the accompanying drawings

Figure 1:
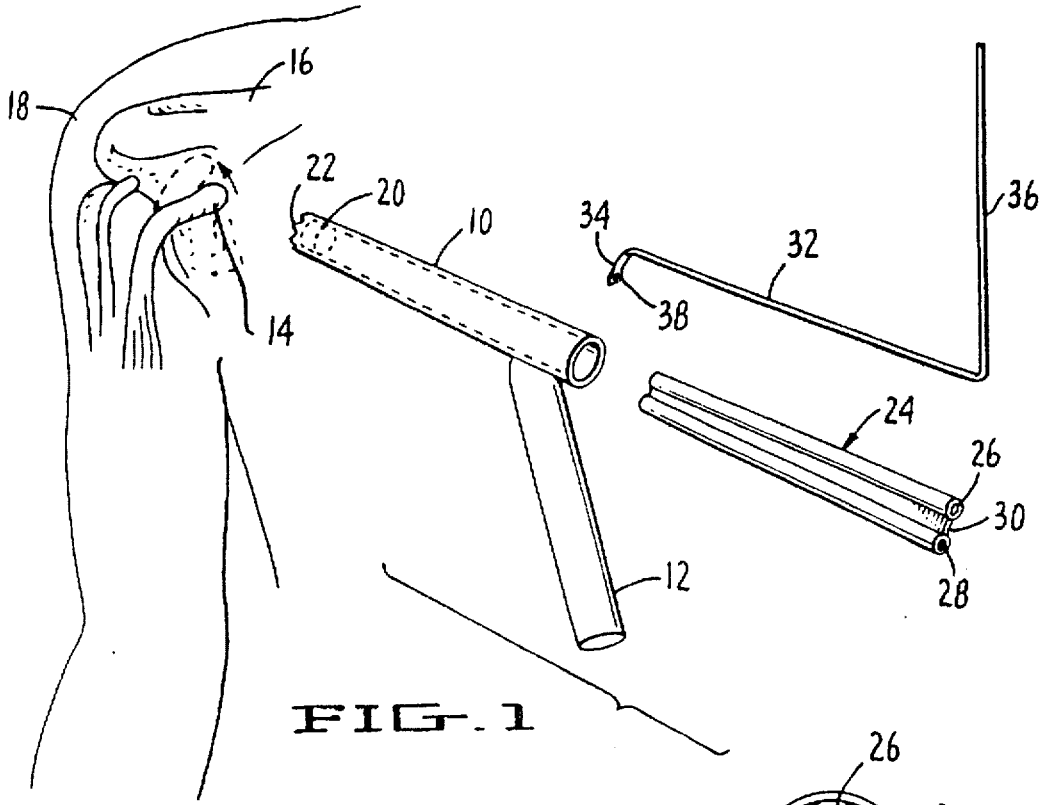
FIG. 1 is an exploded view of the apparatus of this invention with a schematic diagram of a shoulder to which a ruptured tendon is to be attached.
Figure 2:
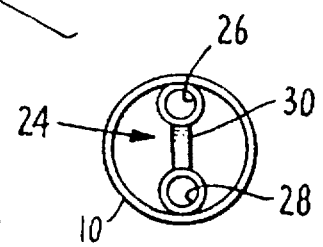
FIG. 2 is a cross sectional view of the cannula with the drill guide in place.
Figure 3:
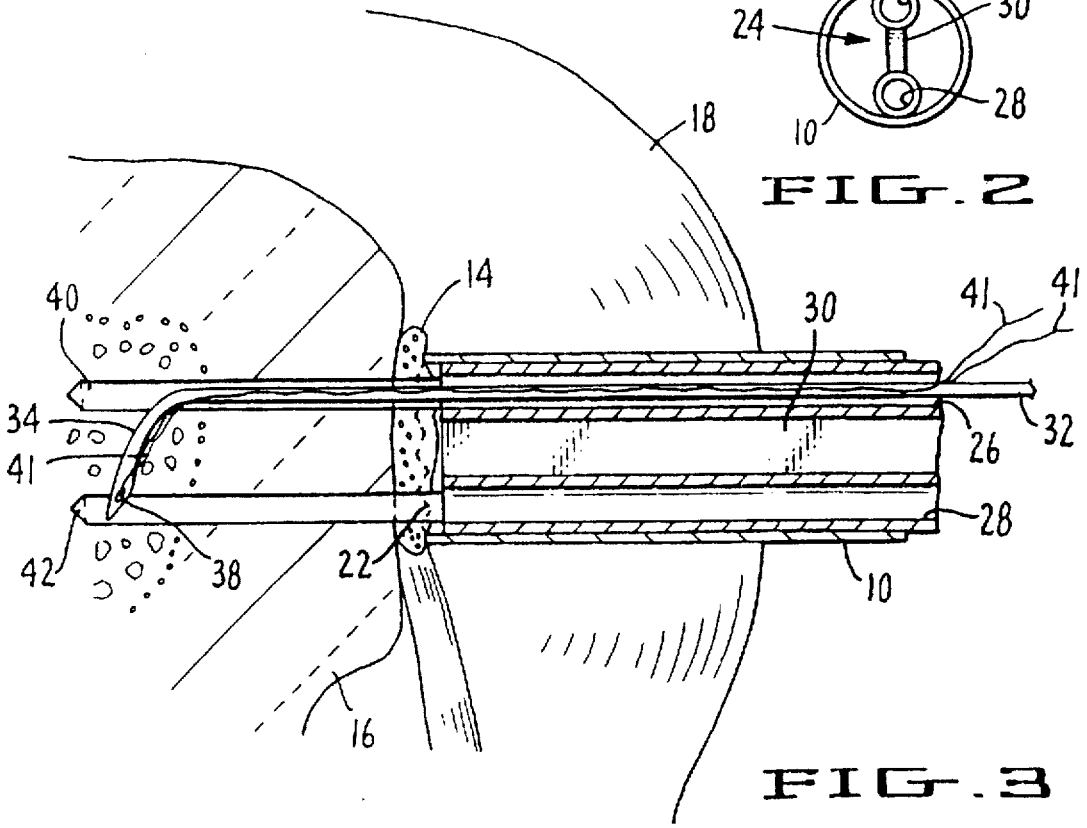
FIG. 3 is a cross sectional view showing all parts assembled as the suture is inserted.
Figure 5:
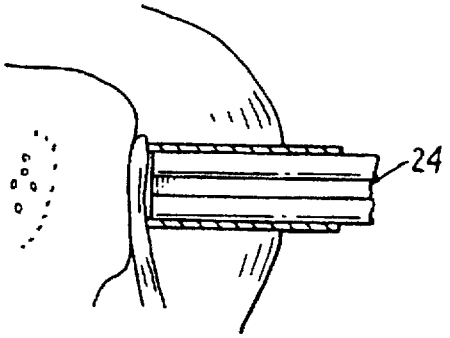
Figure 6:
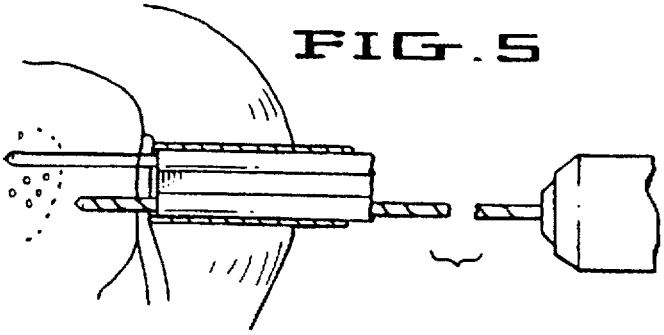
Figure 7:
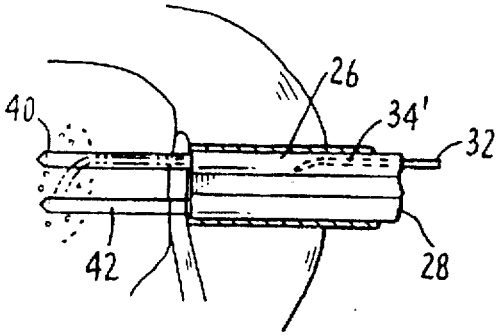
Figure 7A:
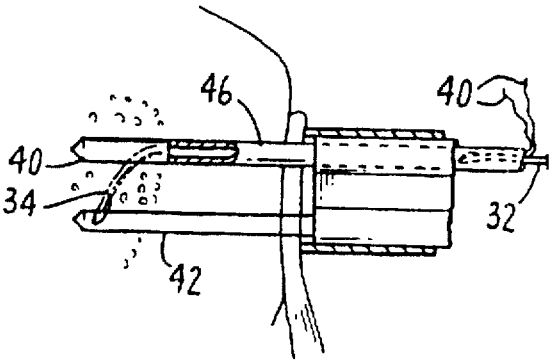
Figure 8:
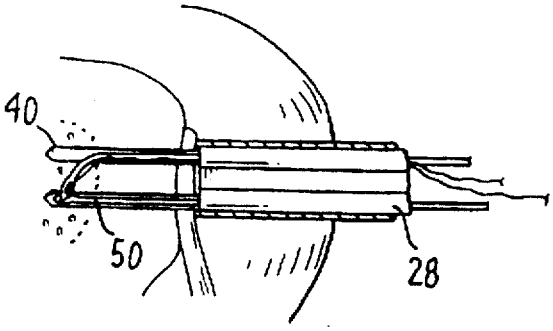
Figure 9:
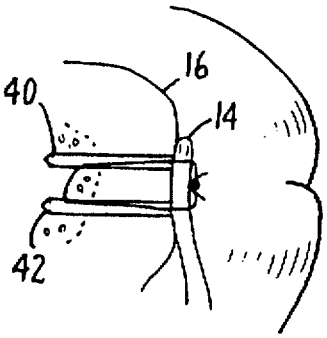
Figure 10:
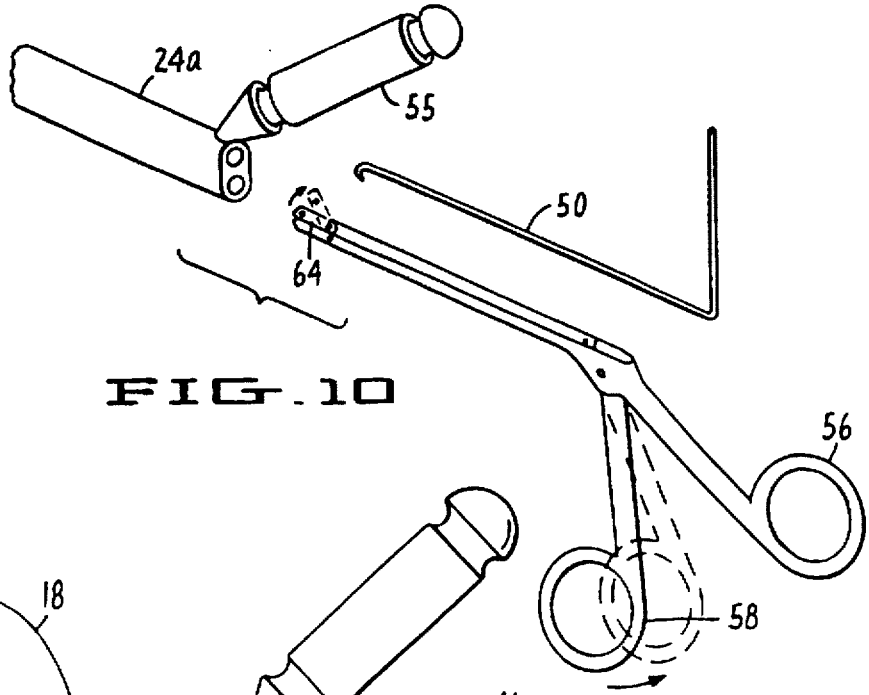
Figure 11:
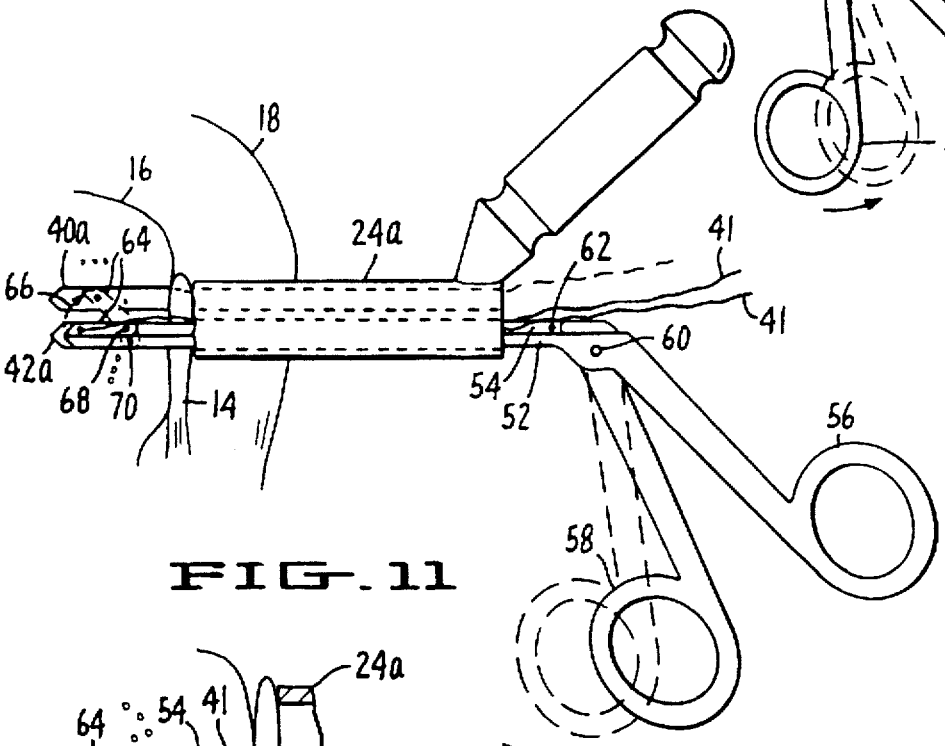
Figure 12:
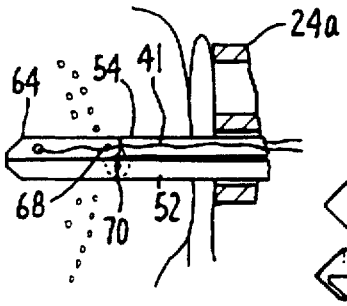
Figure 13:
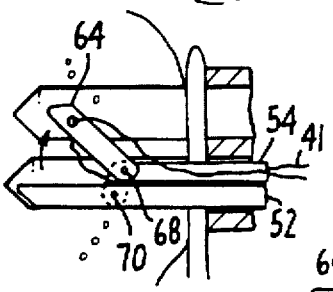
Figure 14:
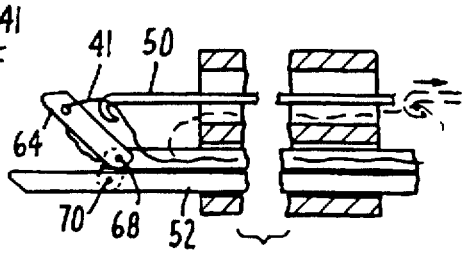

FIGS. 4, 5, 6, 7, 8 and 9 are a series of figures similar to FIG. 3 showing the sequence of steps performed in accordance with the invention, and FIG. 7A illustrates an alternative to FIG. 7; and FIG. 10 is a view similar to FIG. 1 showing an alternative form of apparatus useful in this invention, and FIGS. 11, 12, 13 and 14 are views similar to FIGS. 3, 7 and 8 showing the operation of the apparatus of FIG. 10.

Referring now in detail to the drawings and particularly to FIG. 1 a cannula 10 having a handle 12 is used to form a passageway for arthroscopic surgery to attach a tendon 14 to a bone 16 through overlying soft tissue 18.

The end of the cannula may contain a removable plug 20 to facilitate insertion of the cannula through the soft tissue, and the inner end of the cannula may contain teeth 22 by which the tendon 14 may be grasped by the cannula. A drill guide 24 contains two generally parallel bores 26 and 28 preferably ⅛ inch in diameter separated by a central web 30 ⅛ inch in diameter.

A suture pusher 32 has a central wire stem with a curved end portion 34 projecting laterally from the central stem and a handle portion 36 projecting laterally opposite to the projection 34 on the opposite end of the stem. The suture pusher contains an eye 38 through which a suture 40 is threaded as illustrated in FIG. 3. Preferably the suture pushing end 34 of the suture pusher projects laterally from the stem of the suture pusher by a sufficient distance to penetrate from one hole in the bone to the other as shown in FIG. 3. This lateral projection may be approximately ⅛ inch with the preferred dimensions set forth above for the drill guide.

Figure 4:
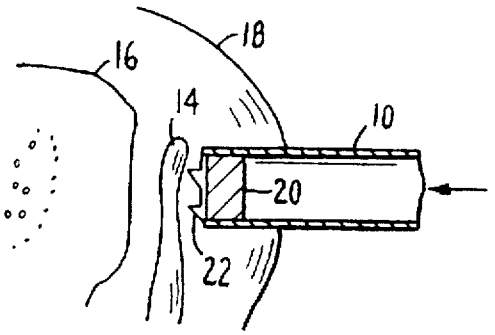

As explained above this apparatus is used as follows: The cannula 7A is inserted into the tissue as illustrated in FIG. 4 until it engages the bone where a suture is to be attached. Where the tendon 14 is to be attached to the bone by the suture the tendon is grasped and held to the bone by the cannula as the cannula is inserted and the drill guide 24 is then inserted as shown in FIG. 5. A drill is then used as shown in FIG. 6 to drill two holes 40 and 42 aligned with the bores 26 and 28 respectively of the drill guide.

A suture 41 is then threaded through the eye 38 in the suture pusher 32 and the suture pusher is forced into the bore 26 of the drill guide which causes the resilient TiNi alloy wire to straighten out resiliently in the bore 26 as illustrated at 34' in FIG. 7. The suture pusher 32 is pushed into the hole 40, and as the tip 34 emerges from the drill guide, the resiliency of the wire forces the tip to move out laterally in a direction opposite the handle 36 and the surgeon orients the handle 36 so that the top 34 moves from the hole 40 to the hole 42.

As illustrated in FIG. 7A a tube 46 may be inserted in the drill guide bore 26 and into the hole 40 to receive and guide the tip 34 to a predetermined depth inside the bone before releasing the tip 34 from its straightened out condition, and a suitable index may be provided on the outer end of the tube 46 for this purpose.

Once the tip 34 penetrates from the hole 40 to the hole 42 as illustrated in FIG. 8, one end of the suture may be retrieved through the drill bore 28 by a suitable suture hook 50.

Finally once the suture has been retrieved out through the bore 28, the suture pusher and the drill guide may be withdrawn. Knots are then tied in the suture and passed down the cannula to attach the tendon 14 to the bone 16, and the excess ends of the suture may be cut off and the cannula withdrawn leaving the suture attached as shown in FIG. 9.

In the alternative shown in FIGS. 10–14, the drill guide **24*a* has a handle 50 and may be used with a cannula as described above. In place of the suture pusher 32 of FIG. 1, the apparatus of FIGS. 10–14 uses a suture pusher which is constructed somewhat like an arthroscopic grabber. Two parallel arms 52 and 54 extend through one bore of the drill guide 24*a*, and operation of the scissors handles 56 and 58 about pivots 60 and 62 slides the arms with respect to each other to cause a suture pushing end 64 to move in the direction of arrow 66 via pivots 68 and 70 to push the suture 41 from one hole 42*a* in the bone to the other hole 40*a***.

While certain details of the invention have been illustrated and described herein it is obvious that many modifications thereof may be made.

I claim:

1. Apparatus for attaching a suture to bone under soft tissue comprising in combination:

a cannula having an inner bore, a drill guide telescopically received in the cannula and having at least two generally parallel bores, and a suture pusher comprising a tool having a straight section telescopically received in one of the bores of the drill guide, a laterally extending handle on one end and on the other end a suture holding section *laterally* movable *relative to the straight section* in response to manipulation of the handle to push a suture loop through soft bone material between two parallel holes in bone aligned with two of the bores in the drill guide.

2. A suture pusher comprising a strand of resiliently deformable wire having a straight section, a laterally extending handle on one end and on the other end an appertured and naturally curved suture pushing section which in unstressed condition extends laterally from the straight section and a sleeve telescopically surrounding the strand of wire and supporting the naturally curved suture pushing section aligned with the straight section whereby the suture pushing section deforms to said unstressed laterally extending condition responsive to manipulation of the handle to move the wire telescopically from the sleeve.

3. The method of attaching a suture to bone under soft tissue which comprises:

inserting a cannula through soft tissue substantially to the bone, inserting into the cannula a drill guide having at least two generally parallel spaced apart bores, drilling two non-intersecting holes aligned with the bores of the drill guide into the bone through the hard surface of the bone into softer inner bone material, inserting through one of the bores and holes a suture pusher having a suture carrying end and pushing the suture carrying end, with a suture loop thereon, through the inner bone material from the one hole to the other hole, retrieving one strand of the suture loop through the other bone hole and bore, removing the pusher and the drill guide, tying a knot in the suture and passing it down the suture through the cannula, and removing the cannula leaving the suture tied to the bone with the suture encircling a bridge of hard surface bone material between the two holes.

4. The method of claim 3, in which the suture pusher is a strand of a resiliently flexible TiNi alloy having a straight section, a laterally extending handle on one end and on the other end a curved suture pushing section extending laterally from the straight section and resiliently deformable to pass through a bore in a generally straightened condition.

5. The method of claim 4 in which a tube is inserted through the one bore and into the one hole in the bone before inserting the suture pusher so that the tube guides the suture pusher down into the bone before pushing the suture from the one hole to the other hole.

*6. Apparatus for attaching a suture to bone under soft tissue, comprising, in combination:*

*a drill guide having at least two generally parallel bores; and*

*a suture pusher having a proximal section and a distal section, the distal section including a suture holding section laterally movable relative to the proximal section in response to manipulation of the proximal section to push a suture loop carried by the distal section through soft bone material between two parallel holes in the bone aligned with two of the bores in the drill guide.*

*7. The apparatus of claim 6 wherein the suture pusher includes a straight section and is formed of resiliently deformable material, and wherein the distal section has an unstressed condition in which it curves laterally away from the straight section.*

*8. A suture pusher comprising:*

*a strand of resiliently deformable wire having a straight section extending between proximal and distal sections, the distal section including a naturally curved suture carrying section which in an unstressed condition extends laterally from the straight section in a direction;*

*a sleeve telescopically surrounding the strand of wire and supporting the naturally curved suture pushing section in approximate alignment with the straight section, whereby the suture pushing section deforms to said unstressed laterally extending condition responsive to*

*manipulation of the proximal section to move the wire telescopically from a distal portion of the sleeve; and*

*means remote from the distal section of the strand for visually indicating the direction in which the distal section will laterally extend when moved from the distal portion of the sleeve.*

*9. The method of attaching a suture to bone under soft tissue which comprises:*

*forming an incision through soft tissue substantially to an underlying bone;*

*inserting into the incision a drill guide having at least two generally parallel spaced apart bores,*

*drilling two non-intersecting holes aligned with the bores of the drill guide into the bone through the hard surface of the bone into softer inner bone material,*

*inserting through one of the holes a suture pusher having a suture carrying end and pushing the suture carrying end, with a suture loop thereon, through the inner bone material from the one hole to the other hole,*

*retrieving one strand of the suture loop through the other bone hole and bore,*

*removing from the incision the suture pusher and the drill guide, and*

*tying a knot in the suture, leaving the suture tied to the bone with the suture encircling a bridge of hard surface bone material between the two holes.*

*10. The method of attaching a suture to bone under soft tissue which comprises:*

*forming an incision through soft tissue substantially to an underlying bone;*

*forming a pair of non-intersecting holes in the bone;*

*inserting a sleeve having at least one bore into the incision,*

*inserting a suture pusher into the sleeve, the suture pusher having a suture carrying end carrying a suture loop,*

*with the suture carrying end of the suture pusher disposed within the sleeve and with the sleeve disposed within the incision and substantially longitudinally aligned with a first one of the holes, advancing the suture carrying end out of the bore and into the inner bone material*

*causing the suture carrying end to push the suture loop from the first hole to a second one of the holes,*

*retrieving a strand of the suture loop through the second hole,*

*removing the suture pusher and sleeve from the incision, and*

*tying a knot in the suture, leaving the suture tied to the bone with the suture encircling a bridge of hard surface bone material between the two holes.*

* * * * *